United States Patent [19]

Yamaguchi et al.

[11] 3,994,175

[45] Nov. 30, 1976

[54] DEVICE FOR DETECTING SPECIFIC GRAVITY AND LEVEL OF LIQUID

[75] Inventors: Hiroaki Yamaguchi, Anjo; Junichiro Naito, Toyokawa, both of Japan

[73] Assignee: Nippon Soken, Inc., Nishio, Japan

[22] Filed: June 18, 1975

[21] Appl. No.: 588,174

[30] Foreign Application Priority Data

June 25, 1974  Japan.............................. 49-72942

[52] U.S. Cl.................................. 73/453; 73/308; 340/249
[51] Int. Cl.²..................... G01N 9/14; G08B 19/00
[58] Field of Search ............ 73/447, 453, 308, 313; 340/59, 244 A, 248 Y, 249; 136/182

[56] References Cited
UNITED STATES PATENTS

| | | | |
|---|---|---|---|
| 1,955,315 | 4/1934 | Styer................. | 73/453 X |
| 1,965,837 | 7/1934 | Herdeg.............. | 340/249 |
| 3,742,342 | 6/1973 | Schick................ | 73/313 |
| 3,777,574 | 12/1973 | Brown et al.......... | 73/453 |

Primary Examiner—James J. Gill
Attorney, Agent, or Firm—Cushman, Darby & Cushman

[57] ABSTRACT

A device for detecting the specific gravity and level of liquid in a container comprising a light source, a photoelectric transducer positioned in light receiving relationship with respect to the light source, a float which has a predetermined specific gravity and is displaced depending upon the change in specific gravity and level of the liquid, and means operatively coupled to the float so as to permit or interrupt the light transmission from the light source to the photoelectric transducer.

9 Claims, 4 Drawing Figures

DEVICE FOR DETECTING SPECIFIC GRAVITY AND LEVEL OF LIQUID

BACKGROUND OF THE INVENTION

The present invention relates to a device for detecting the specific gravity and level of liquid in a container, and especially of the electrolyte in a storage battery.

In the typical conventional device for detecting the specific gravity and liquid level of the electrolyte in a storage battery, a reed switch is so arranged as to be turned on or off by a magnet embedded in a float which is displaced in the electrolyte, depending upon the change in specific gravity and/or liquid level thereof. However, such conventional detecting device has a disadvantage that the specific gravity and liquid level cannot be precisely detected, since, unless the specific gravity and the level change beyond some extent of their ranges, the float cannot move, overcoming an attracting force between the reed switch and the magnet embedded in the float.

SUMMARY OF THE INVENTION

The present invention was made to eliminate the above disadvantage and has for its object to provide a device for detecting the specific gravity and level of liquid with a greater degree of accuracy, in which a float without a magnet is so arranged as to permit or interrupt the light transmission from a light source to a photoelectric transducer depending upon the change in specific gravity and/or liquid level.

The present invention is characterized in that a detector circuit, comprising a light source and a photoelectric transducer, is disposed in a housing in compact manner and has a single lead wire for serving both to receive an input current from a power supply and to send an output signal. The circuit detects the conditions of the specific gravity and liquid level of the liquid in a form of a current signal level (or current ratio). The resultant advantages of the invention are that:

1. the number of lead wires to be connected to the detector is reduced; and
2. the detection in the form of a current signal level is advantageous in that the output impedance of the detector circuit is less and the noises are hardly superimposed upon the signal so that the detection at a remote place is facilitated.

DESCRIPTION OF THE PREFERRED EMBODIMENT

Figure 1A:
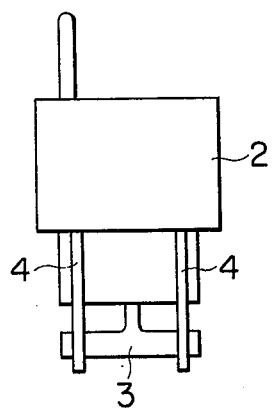
FIGS. 1(a) and 1(b) are schematic front and bottom views of one preferred embodiment of the present invention.
Figure 1B:
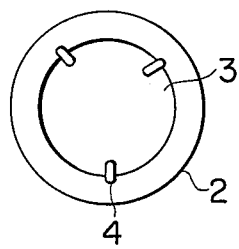
Figure 2:
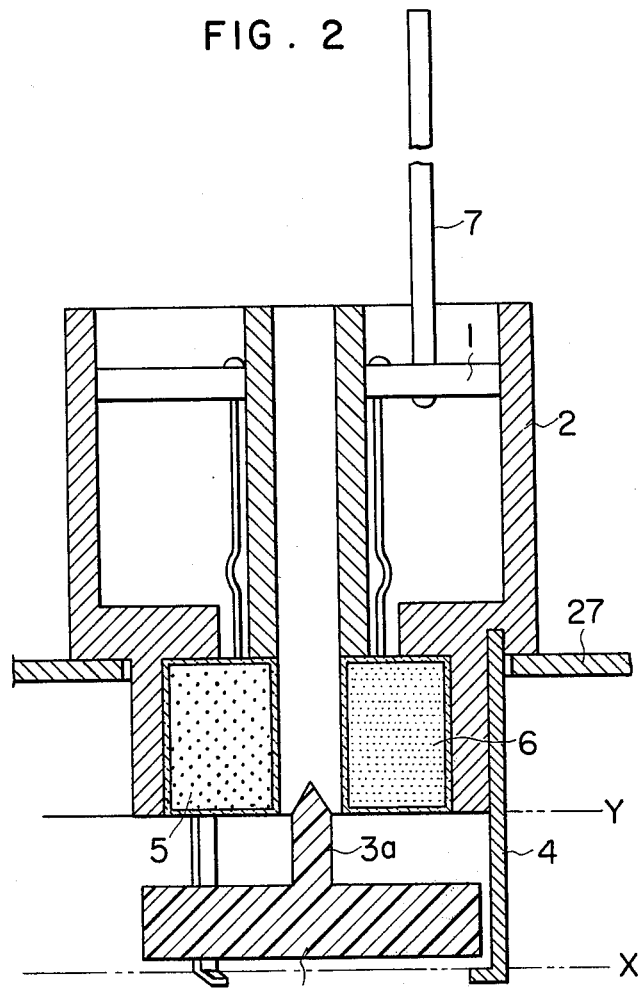
FIG. 2 is a sectional view, on enlarged scale, thereof.

The present invention will be described in a preferred embodiment, wherein a device according to the present invention is adapted to be applied for detecting changes in the specific gravity and level of an electrolyte filled in a battery container which is mounted on a vehicle. Referring to FIGS. 1 and 2, reference numeral 1 denotes a printed circuit board electrically connected through a lead wire 7 to a converter circuit which converts a current signal into a voltage signal, and which will be referred to as a current-to-voltage convention in this specification for brevity and be described in detail hereinafter. Reference numeral 2 denotes a housing; 3, a float which displaces itself in the electrolyte, depending upon the change in both specific gravity and liquid level thereof and has a predetermined specific gravity (for instance 1.19 ) slightly greater than the specific gravity 1.10 of the electrolyte which is shown as the battery is over-discharged; 3a, a light shielding member formed integral with the float 3; 4, three float guide rods having a relatively small diameter so as to minimize the adverse effects due to the friction, surface tension and any other factors which resist the displacement of the float 3; 5, a light emitting diode of the type which emits light when the forward current flows therethrough; 6, a phototransistor so positioned as to receive the light emitted from the light emitting diode 5; and 27, a container of the battery in which is mounted the detecting device having the above-said construction in such a way that the float 3 may be immersed in the electrolyte. In general, the battery container 27 is divided into a plurality of small chambers or cells by separator plates, not shown, however, each electrolyte in each cell generally changes its electrolytic condition in the same manner as the other so that it is sufficient to provide in only one cell the detecting device having the above-said construction.

Figure 3:
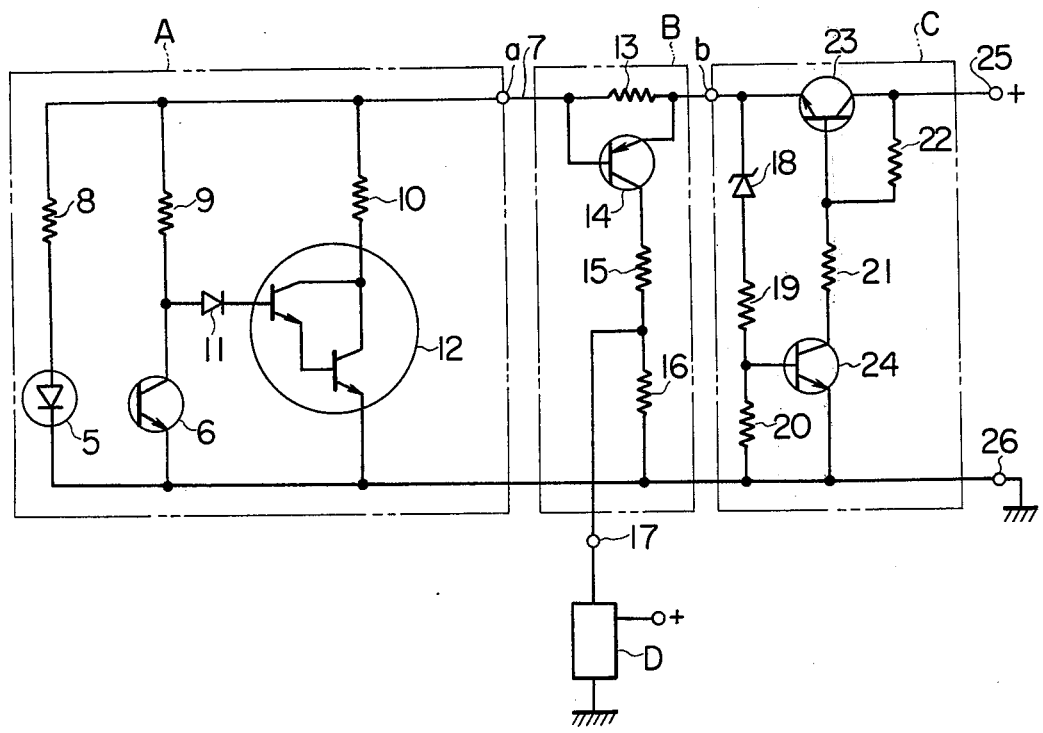
FIG. 3 is a diagram of an electrical circuit thereof.

Referring to FIG. 3, the electrical circuit of the device will be described. Reference character A denotes the electrical circuit of the detector device for detecting the specific gravity and liquid level of the electrolyte, said circuit being adapted to convert their value into electrical current B, the current-to-voltage converter for converting the current output signal from the circuit A into the voltage signal, said converter being possibly arranged in the vehicle compartment; C, a constant voltage circuit or voltage regulator for supplying a regulated voltage to the circuits A and B; D, an alarm circuit. The detector circuit A comprises resistors 8, 9 and 10, the light emitting diode 5, the phototransistor 6, two NPN transistors 12 in Darlington connection, and a diode 11 preventing malfunctions due to unwanted external lights. The current-to-voltage converter B comprises a resistor 13 converting the current signal into the corresponding voltage signal, a transistor 14 detecting the voltage across the resistor 13, a voltage divider consisting of resistors 15 and 16 which put out the changes in the specific gravity and liquid level, and an output terminal 17 connected to the alarm circuit D. The voltage regulator C comprises a zener diode 18 which, when the voltage exceeds a predetemined value, flows the current reversely, resistors 19, 20, 21 and 22, transistors 23 and 24, a terminal 25 connected to a positive power supply terminal and a terminal 26 grounded. Since the voltage regulator of the type shown in FIG. 3 is well-known in the art, no detailed description thereof will be made in this specification.

The mode of operation will be described. In FIGS. 2 and 3, the detecting device or detector A is so mounted in the container of the battery that the bottom of the light emitting diode 5 is positioned at the same level Y, shown in FIG. 2, as the normal liquid level of the electrolyte. It is assumed that when the level of the electrolyte drop to the level X, the quantity of the electrolyte is not sufficient. First, the operation of detecting the specific gravity will be described. Since the float 3 has a predetermined specific gravity, it rises or sinks depending upon the change in the specific gravity of the electrolyte which is effected upon the condition or charge of the battery. The specific gravity of the electrolyte is low when the battery is less charged, but the specific gravity is increased when the battery is fully charged, it finally reaches the maximum value of for instance 1.260 when the battery is fully charged. Therefore, the specific gravity of the float 3 is determined at a slightly higher value, for example 1.19, than that of 1.10 of electrolyte which value shows the overdischarge condition of the battery. The value of 1.19 of the electrolyte is such condition that the battery charge is necessary. Therefore, when the quantity of the electrolyte is sufficient and the battery is sufficiently changed, for instance enough to drive a starter, the float 3 is at the level Y where the light shielding projection 3a is positioned between the light emitting diode 5 and the phototransistor 6.

Unregulated D.C. voltage applied to a terminal 25 is regulated to a predetermined regulated voltage by means of the voltage regulator C. The regulated voltage is applied through the resistor 13 to one end of each resistor 8, 9 and 10 so that the light emitting diode 5 emits the light having a constant energy. When the light shielding projection 3a interrupts the light transmitted from the diode 5 to the phototransistor 6, the latter is cut-off. As a result, the current flows through the diode 11 to the base of the first transistor in 12 and in turns on the same.

When the specific gravity of the electrolyte is lower, as the battery is discharged, than that of the float 3, the latter sinks so that the light shielding projection 3a is moved away from the space between the light emitting diode 5 and the phototransistor 6. The light from light emitting diode 5 is received by the phototransistor 6 so that the latter is turned on. The base potential of the first transistor in 12 drops so that the latter is turned off. The value of the collector resistor 10 is selected 1/6 to 1/10 of the value of the parallel-connected resistors 8 and 9. Therefore, the following relation is concluded between the two current values which are measured at a point $a$ when the phototransistor 6 is turned-on or turned-off, corresponding when the float 3 is raised or lowered.

current with the float in raised position/current with the float in lower position = 6 to 10

The means that the change in specific gravity may be detected in the form of the current. Therefore the lead wire 7 may be used not only as a signal transmission line but also a power supply line so that the detection at a remote place may be facilitated.

The current output signal at the point $a$ is converted into the voltage output signal by means of the current-to-voltage converter B. That is, the voltage across the resistor 13 changes depending upon the current flowing therethrough. When the float 3 is in the lower position, the current at the point $a$ is less so that the voltage drop across the resistor 13 is also small. As a result, the forward bias voltage between the emitter and base of the transistor 14 is too low to turn on the transistor 14. Therefore the potential at the output terminal 17 which is connected to the junction between the resistors 15 and 16 is zero or ground potential.

On the other hand when the float 3 is in the raised position, the NPN transistors 12 are in the conductive state so that the current measured at the point $a$ is increased 6 to 10 times. As a result, the voltage drop across the resistor 13 is sufficient to turn on the transistor 14. Therefore the voltage output signal whose value is dependent upon the values of the voltage divider resistors 15 and 16 is obtained at the output terminal 17. This means that when the float 3 is in the raised position or when the specific gravity of the electrolyte is above a predetermined value, the output signal of a predetermined voltage appears at the output terminal 17. However, when the float 3 is in the lowered position or when the specific gravity of the electrolyte is less than a predetermined value, the potential at the output terminal 17 is zero. Thus, the change in the specific gravity of the electrolyte may be detected. In response to the voltage output signal at the terminal 17, the alarm circuit D which is installed in the compartment of the vehicle is actuated to give visual or audible alarm signal.

Next, the measurement of the liquid level of the electrolyte will be described. Even when the specific gravity of the electrolyte is higher than a predetermined value, when the liquid level of the electrolyte drops to the level X in figure A due to the vaporization of the electrolyte, the float 3 is lowered so that the light shielding projection 3a is moved away from the space between the light emitting diode 5 and the phototransistor 6. Therefore, the phototransistor 6 is turned on, and the drop of the liquid level of the electrolyte may be detected in a manner substantially similar to that described above. Thus, according to the present invention, the change in both the specific gravity and liquid level of the electrolyte may be detected as a change in potential at the output terminal 17.

In the instant embodiment, the float 3 having a specific gravity 1.19 is made of rubber (mixture of SBR and NR), and the electrolyte has a specific gravity of 1.25 when the battery is fully charged while the specific gravity drops to 1.10 when the battery is completely discharged. The float 3 may be made of any suitable material as far as it may have a predetermined specific gravity. In the instant embodiment, the light emitting diode 5 is used, but it is easily understood that instead of the light emitting diode any suitable light emitting means such as a lamp may be used. Instead of the phototransistor 6 which converts the light signal into the electrical signal, a photoconductive cell whose resistance varies in response to the intensity of light impinged thereupon may be used. Instead of forming the light shielding projection 3a integral with the float 3, the former may be fabricated as a separate part and may be attached to the latter. Furthermore the float 3 may be so arranged that it may be interposed or withdrawn between the light emitting diode 5 and the phototransistor 6.

As described above, according to the present invention, the float with a predetermined specific gravity is so arranged as to be displaced into or out of between the light source and photoelectric element in order to control the light transmission therebetween. Unlike the conventional systems, the float is not influenced by the attracting force of a magnet so that the displacement of the float may immediately take place in response to the change in both the specific gravity and level of the liquid, thus resulting in the precise detection of the specific gravity and liquid level.

What is claimed is:
1. A device for detecting both the specific gravity and liquid level of liquid in a container; comprising
   a. a light source;

b. a photoelectric transducer means disposed in opposed relation with said light source for generating an electrical signal representing the intensity of light received from said source;

c. a float having a predetermined specific gravity and displaceable in response to change in both specific gravity and liquid level of said liquid, said float comprising a light shielding means which, when the specific gravity and liquid level of said liquid are above respective predetermined values, rises to interrupt light transmission between said light source and said photoelectric transducer means and which, when at least one of the specific gravity and liquid level of said liquid is lower than its predetermined value, falls to permit the light emitted from said light source to reach said photoelectric transducer means;

d. a detector circuit disposed in a housing together with said light source and said photoelectric transducer means for sending a current output signal in response to the electrical signal from said photoelectric transducer means through an output line which also serves to receive an input current from a source of electricity; and e. a current-to-voltage converter circuit connected to said output line of said detector circuit for converting the current output signal from said detector circuit into a voltage output signal representing conditions of the specific gravity and liquid level of said liquid.

2. A device as set forth in claim 1, wherein said housing is provided with a means for guiding said float.

3. A device as set forth in claim 1, wherein said container is that of a battery and wherein said device detects the specific gravity and liquid level of the electrolyte of said battery.

4. A device as set forth in claim 1, further comprising an alarm circuit connected to said current-to-voltage converter circuit and responsive to the voltage level of the voltage output signal from said converter circuit.

5. A device as set forth in claim 1, wherein said light source comprises a light emitting diode and wherein said photoelectric transducer means comprises a phototransistor.

6. A device as set forth in claim 1, wherein said detector circuit includes an amplifier circuit for amplifying the output signal of said photoelectric transducer means to send the amplified signal as a current output signal through said output line.

7. A device as set forth in claim 1, wherein said current-to-voltage circuit comprises a first resistor connected in series to said output line of the detector circuit for detecting the level of said current output signal, a transistor circuit having a base-emitter circuit which is connected in parallel to said first resistor, and a second resistor connected to an emitter-collector circuit of said transistor circuit for generating the voltage output signal corresponding to said current output signal from the said detector circuit.

8. A device for detecting both the specific gravity and liquid level of liquid in a container, comprising:

a. a light source;

b. a photoelectric transducer means disposed in opposed relation with said light source for generating an electrical signal representing the intensity of light received from said source;

c. a float having a predetermined specific gravity and displaceable in response to change in both specific gravity and liquid level of said liquid, said float comprising a light shielding means which, when the specific gravity and liquid level of said liquid are above respective predetermined values, rises to interrupt light transmission between said light source and said photoelectric transducer means and which, when at least one of the specific gravity and liquid level of said liquid is lower than its predetermined value, falls to permit the light emitted from said light source to reach said photoelectric transducer means;

d. a detector circuit disposed in a housing together with said light source and said photoelectric transducer means for generating a current output signal in response to the electrical signal from said photoelectric transducer means;

e. a current-to-voltage converter circuit connected to said detector circuit and comprising a transistor circuit for converting the current output signal from said detector circuit into a voltage output signal; and f. an alarm circuit connected to said current-to-voltage converter circuit and actuable to give an alarm signal when the voltage level of said voltage output signal reaches a predetermined value.

9. A device for detecting both the specific gravity and liquid level of liquid in a container; comprising a. a light source;

b. a photoelectric transducer means disposed in opposed relation with said light source for generating an electrical signal representing the intensity of light received from said source;

c. a float having a predetermined specific gravity and displaceable in response to change in both specific gravity and liquid level of said liquid, said float comprising a light shielding means which, when the specific gravity and liquid level of said liquid are above respective predetermined values, rises to interrupt light transmission between said light source and said photoelectric transducer means which, when at least one of the specific gravity and liquid level of said liquid is lower than its predetermined value, falls to permit the light emitted from said light source to reach said photoelectric transducer means;

d. a detector circuit disposed in a housing together with said light source and said photoelectric transducer means for amplifying the electrical signal from said photoelectric transducer means and sending the amplified signal as a current output signal through an output line which also serves to receive an input current from a source of electricity;

e. a current-to-voltage converter circuit connected to said detector circuit and comprising a resistor connected in series to said output line of the detector circuit for detecting the level of said current output signal, and a transistor circuit for generating a voltage output signal corresponding to the level of said current output signal by detecting the voltage drop of said current output signal across said resistor; and f. an alarm circuit connected to said current-to-voltage converter circuit and actuable to give an alarm signal when the voltage level of said voltage output signal reaches a predetermined level.

* * * * *